United States Patent

Bugaut et al.

[11] 4,305,717
[45] Dec. 15, 1981

[54] METAPHENYLENEDIAMINES IN DYEING COMPOSITIONS FOR KERATINIC FIBERS

[75] Inventors: Andree Bugaut, Boulogne; Jean-Jacques Vandenbossche, Aulnay, both of France

[73] Assignee: L'Oreal, Paris, France

[21] Appl. No.: 722,485

[22] Filed: Sep. 13, 1976

[30] Foreign Application Priority Data

Aug. 20, 1976 [FR] France .................. 76 25385

[51] Int. Cl.³ .............................................. A61K 7/13
[52] U.S. Cl. .................................... 8/411; 8/401; 8/414; 8/115; 8/116; 8/421; 8/424; 564/166; 564/161
[58] Field of Search ............. 260/558 A; 8/10.2, 11, 8/32, 407, 411

[56] References Cited

U.S. PATENT DOCUMENTS

| | | | |
|---|---|---|---|
| 2,374,337 | 4/1945 | Dickey et al. | 260/558 A |
| 3,200,040 | 8/1965 | Lange | 8/10.2 |
| 3,658,454 | 4/1972 | Paul | 260/558 A X |
| 3,816,529 | 6/1974 | Loffelman | 260/558 A |
| 3,884,627 | 5/1975 | Brody et al. | 8/10.2 |

Primary Examiner—Natalie Trousof
Assistant Examiner—Vera C. Clarke
Attorney, Agent, or Firm—Brisebois & Kruger

[57] ABSTRACT

Dye compositions comprising a coupler having to the formula

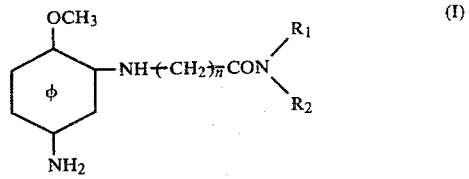

(I)

in which formula $R_1$ and $R_2$ are identical or different and represent a hydrogen atom or an alkyl radical having 1 to 2 carbon atoms and n represents a number equal to 1 or 2 and a paraphenylenediamine.

This coupler is particularly suitable for use in a dyeing composition comprising paraphenylenediamines responding to the formula

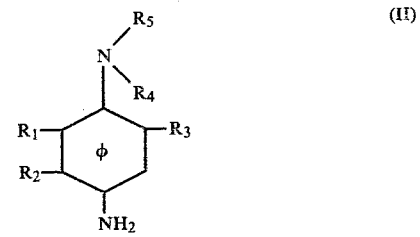

(II)

or the corresponding acid salts; formula in which $R_1$, $R_2$ and $R_3$ are identical or different and represent a hydrogen atom, an alkyl or alkoxy radical having 1 to 2 carbon atoms, $R_4$ and $R_5$ are identical or different and represent a hydrogen atom, a alkyl radical, hydroxyalkyl, alkoxyalkyl in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 carbon atoms, with the reservation that $R_1$ or $R_3$ represents hydrogen when $R_4$ and $R_5$ do not represent a hydrogen atom.

14 Claims, No Drawings

METAPHENYLENEDIAMINES IN DYEING COMPOSITIONS FOR KERATINIC FIBERS

It is known that, in the field of dyeing keratinic fibers and, in particular hair, the metaphenylenediamines which form part of the class of compounds currently called "couplers", play an important part.

In effect, the association of metaphenylenediamines with paraphenylenediamines gives rise, in an alkaline oxidizing medium, and more particularly, in the presence of hydrogen peroxide, to indamines capable of imparting to the keratinic fibers very deep blue colorations. This color is indispensable in formulations in order to obtain not only black, grey, but even certain burnt or copper chestnuts.

Despite its important role, this category of couplers has heretofore been limited in practice to a very restricted number of compounds. This overly restricted number is explained by the fact that one may retain for capillary dyeing only, on the one hand, those compounds having a good innocuousness and, on the other hand, the compounds permitting to obtain, on keratinic fibers, blue shades which do not evolve in the course of time.

This instability of the shades obtained is due to easy cyclization into red azine of the indamine blue formed in situ during the oxidation dyeing. The azine formed then undergoes a rapid photochemical degradation in the light, which explains that the hair colored blue reddens rapidly in the shade in a humid atmosphere, whereas it turns green and then yellow in the light. This is particularly the case with the following compounds: metatoluylenediamine; 4-amino-2-amino-N-($\beta$-hydroxyethyl)-1-methyl benzene; 4-amino-2-amino-N-($\beta$-hydroxyethyl)-1-methoxy benzene; 4-amino-2-amino-N-methyl-1-methoxy benzene; 4-amino-N-methyl-2-amino-1-methoxy benzene.

The present invention thus produces new chemical compounds used as couplers which, in association with a large number of paraphenylenediamines in an oxidizing alkaline medium are capable of imparting to keratinic fibers blue shades which are stable to the light, to inclement weather, and to shampooings, and which, moreover, are innocuousness.

The present invention produces the new industrial product which consists of a chemical compound of formula (I)

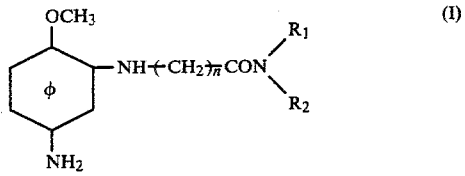

in which formula $R_1$ and $R_2$ are identical or different and represent a hydrogen atom or an alkyl radical having 1 to 2 carbon atoms and n represents a number equal to 1 or 2, $R_1$ and $R_2$ not representing simultaneously hydrogen when n is equal to 2.

The present invention also produces the new industrial product which consists of a dyeing composition for keratinic fibers and, in particular for hair, said composition containing in aqueous solution, at least one paraphenylenediamine as oxidation base, characterized by the fact that it contains, as coupler, at least one compound of formula (I).

In a general way, one may use as oxidation base in the dyeing composition according to the invention paraphenylenediamines of the general formula (II):

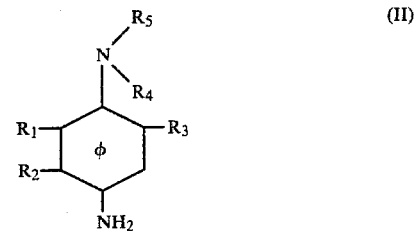

or the corresponding acid salts; formula in which $R_1$, $R_2$ and $R_3$ are identical or different and represent hydrogen, alkyl or alkoxy having 1 to 2 carbon atoms, $R_4$ and $R_5$ are identical or different and represent hydrogen, alkyl, hydroxyalkyl, alkoxyalkyl in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 carbon atoms, with the reservation that $R_1$ or $R_3$ represents hydrogen when $R_4$ and $R_5$ do not represent hydrogen.

The dyeing compositions according to the invention which contain as couplers the compounds of formula (I) and as oxidation base, the compounds of formula (II) impart to keratinic fibers a blue coloration of good quality, that is to say, stable to light, to inclement weather and to shampooing. The compounds of formula (I) give notably blue shades of very good stability with the following oxidation bases:
paraphenylenediamine;
paratoluylenediamine;
2,6-dimethyl-3-methoxy paraphenylenediamine;
2-methyl-5-methoxy paraphenylenediamine;
2,6-dimethyl paraphenylenediamine;
4-amino-N-methoxyethyl aniline;
4-amino-N,N-di-$\beta$-hydroxyethyl aniline;
4-amino-N-ethyl-N-carbamylmethyl aniline, and
4-amino-N-ethyl-N-mesylaminoethyl aniline.

It should be pointed out that the paraphenylenediamines possess a chlorine or fluorine atom on the ring, giving with the compounds of formula (I) violet colorations which rapidly lose their chromaticity in light. This is the case, for example, with 4-amino-N-$\beta$-hydroxyethyl-3-chloro aniline or 4-amino-N-$\beta$-hydroxyethyl 3-fluoro aniline. It should also be pointed out that the paraminophenols used as oxidation base lead, in association with the compounds of formula (I), to a purple red coloration of the keratinic fiber, a coloration which has the disadvantage of rapidly turning yellow.

The dyeing compositions of the invention may also contain, in addition to the coupler or couplers of formula (I) and the associated oxidation base or bases of formula (II) the following products taken singly or in combination:

(1) Other known couplers, for example, resorcin, metaaminophenol, 2-methyl-5-amino phenol, 5-amino-N-$\beta$-hydroxyethyl 2-methyl phenol, 6-hydroxy benzomorpholine, 2,6-dimethyl-5-acetylamino phenol, 2-methoxy-5-carbethoxyamino phenol, 2-methyl-5-ureido phenol, 3-amino-4-methoxy phenol, the dihydrochloride of (2,4-diamino) phenoxyethanol, the dihydrochloride of (2-amino-4-amino-N-methyl phenoxyethanol, the dihydrochloride of (2,4-diamino) phenyl-β-methoxyethylether, the dihydrochloride of (2,4-diamino) phenyl-mesylaminoethylether;

(2) The leucoderivatives of indoanilines and indophenols such, for example, as 4,4'-dihydroxy-2-amino-5-methyl diphenylamine, 4,4'-dihydroxy-2-amino-N-β-hydroxyethyl-5-methyl-2'-chloro diphenylamine, 2,4'-diamino-4-hydroxy-5-methyl diphenylamine;

(3) The polyaminophenols, the monoaminodiphenols, the diaminodiphenols, the polyphenols such as trihydroxybenzene;

(4) Direct dyes and preferably nitrated dyes of the benzene series such as 1-amino-N,N-dihydroxyethyl-3-nitro-4-amino-N'-methyl benzene.
1-amino-N,N(methyl-β-hydroxyethyl)-3-nitro-4-amino-N'-β-hydroxyethyl benzene;
1-amino-N,N(methyl-β-hydroxyethyl)-3-nitro-4-amino-N'-methyl benzene;
1-amino-N-methyl-3-nitro-4-amino-N'-β-hydroxyethyl benzene;
3-nitro-4-amino-N-β-hydroxyethyl anisole,
3-nitro-4-amino-N-β-hydroxyethyl phenol,
(3-nitro-4-amino) phenoxyethanol,
(3-nitro-4-amino-N-methyl) phenoxyethanol,
2-β-hydroxyethylamino-5-nitro anisole,
2-methyl-4-nitro aniline;

(5) Various usual additives such as penetrating agents, foaming agents, thickening agents, anti-oxidizing agents, alkalizing agents, perfumes, sequestrating agents, and film forming products.

The pH of the dying compositions of the invention is between 8 and 11.5. Among the alkalizing agents which may be used, one may cite ammonia, alkylamines such as ethylamine or triethylamine, the alkanolamines such as the mono-, di-, or triethanolamine, sodium phosphate, sodium carbonate. The composition according to the invention may also contain acidifying agents such as phosphoric, lactic, and acetic acid, etc.

One may also add to the composition according to the invention hydrosoluble anionic, cationic, non-ionic, amphoteric, or surface-active agents. Among the surface-active agents particularly usable, one may mention the alkylbenzenesulfonates, the alkylnaphthalenesulfonates, the sulfates, ether sulfates and sulfonates of fatty alcohols, the quaternary ammonium salts such as triethyl cetylammonium bromide, cetyl pyridinium bromide, the diethanolamides of fatty acids, the polyoxyethylenated acids and alcohols and the polyoxyethylenated alkylphenols. Preferably, the surface-active products are present in the composition according to the invention in a proportion comprised between 0.5 and 30% by weight and preferably between 4 and 25% by weight.

One may also add to the composition according to the invention organic solvents for solubilizing compounds which are not sufficiently soluble in water. Among the solvents which may advantageously be used one may mention, by way of example, ethanol, isopropanol, glycerin, glycols such as butylglycol, ethylene glycol, propylene glycol, monoethylether and monomethylether of diethylene glycol and analogous products. The solvents may advantageously be present in the composition in a proportion going from 1 to 40% by weight and preferably comprised between 5 and 30% by weight. The thickening agents which may be added to the composition according to the invention may advantageously be taken in the group formed by sodium alginate, gum arabic, the derivatives of cellulose such as methylcellulose, hydroxyethylcellulose, hydroxypropyl methylcellulose, the sodium salt of carboxymethylcellulose and the polymers of acrylic acid. One may also use mineral thickening agents such as bentonite. Preferably the thickening agents are present in a proportion comprised between 0.5 and 5% by weight in proportion to the total composition and preferably between 0.5 and 3% by weight.

The anti-oxidizing agents which may be added to the composition may include sodium sulfite, thioglycolic acid, sodium acid sulfite, ascorbic acid, and hydroquinone. These anti-oxidizing agents may be present in the composition in a proportion between 0.5 and 1% by weight in proportion to the total weight of the composition.

The dyeing composition according to the invention may contain oxidation agents such as hydrogen peroxide, urea peroxide, or persalts such as ammonium persulfate.

In a general way the compounds of formula (I) are present in the dyeing composition according to the invention in a proportion between 0.0025 and 2.5% by weight in proportion to the total weight of the composition.

The dyeing composition according to the invention may take the form of a liquid solution, a paste, a cream, a gel or any other appropriate form for making a dye for keratinic fibers. In order that the object of the invention may be better understood, there will now be described, by way of purely illustrative and non-limiting examples, the preparation of two compounds of formula (I) and the use of these compounds in dyeing compositions according to the invention.

EXAMPLE 1

Preparation of 2-carbamylmethylamino-4-amino anisole

This preparation comprises two steps represented by the following reaction formulas:

First step:

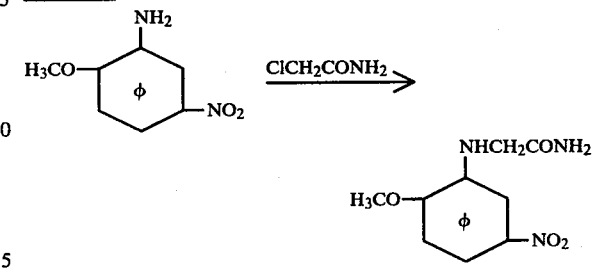

Second step:

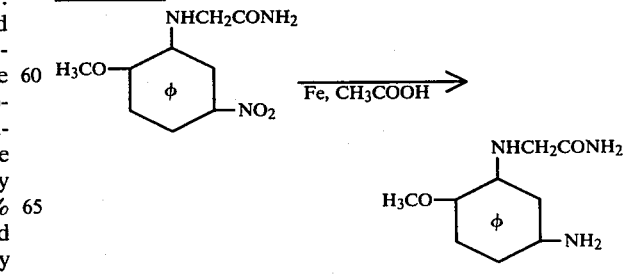

First step

Preparation of 2-carbamylmethylamino-4-nitro anisole

In 2.7 liters of hydroalcoholic solution (⅔ alcohol, ⅓ water), one adds 2.1 mols (353 g) of 2-amino-4-nitro anisole, 2.1 mols (210 g) of calcium carbonate and 4.2 mols (393 g) of chloroacetamide. The mixture is brought to reflux for 64 hours and then drained while boiling. The precipitate which contains the expected product mixed with mineral salts is agitated in 1 liter of water at a temperature of 80° C. Hydrochloric acid is added in a quantity sufficient to destroy calcium carbonate. The expected product is drained, washed two times in boiling water, and recrystallized in acetic acid. After vacuum drying the product melts at 224° C.

The analysis of the product gives the fllowing results:

|   | Calculated for $C_9H_{11}N_3O_4$ | Found |
|---|---|---|
| C % | 48.00 | 48.07 |
| H % | 4.89 | 4.92 |
| N % | 18.67 | 18.50 |

Second step

Preparation of 2-carbamylmethylamino-4-amino anisole

Into 180 ml of water one adds 45 g of powdered iron and 15 ml of acetic acid. One brings this mixture under agitation to a temperature of 85° C. then one adds, little by little, 0.2 mol (45 g) of 2-carbamylmethylamino-4-nitro anisole. One maintains the reaction mixture for 10 minutes at 90° C. One adds soda to obtain a pH of 7.5, and then filters it hot. The filtrate is cooled to a temperature of 0° C. The expected product which precipitates is drained, washed with very little water, dried, recrystallized in methylisobutylketone. It melts at 144° C.

Analysis gives the following results:

|   | Calculated for $C_9H_{13}N_3O_2$ | Found |
|---|---|---|
| C % | 55.39 | 55.50 |
| H % | 6.67 | 6.98 |
| N % | 21.54 | 21.72 |

EXAMPLE 2

Preparation of 2-diethylcarbamylmethyl anisole

This preparation comprises two steps represented by the following reaction formulas:

First step:

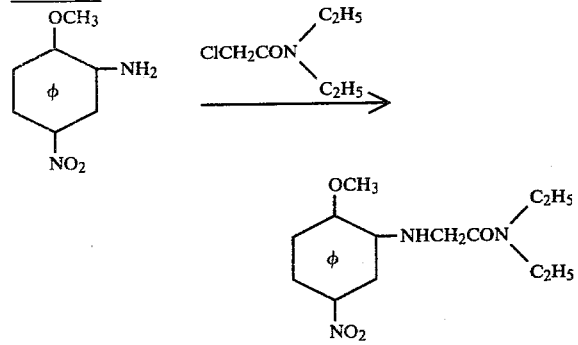

Second step:

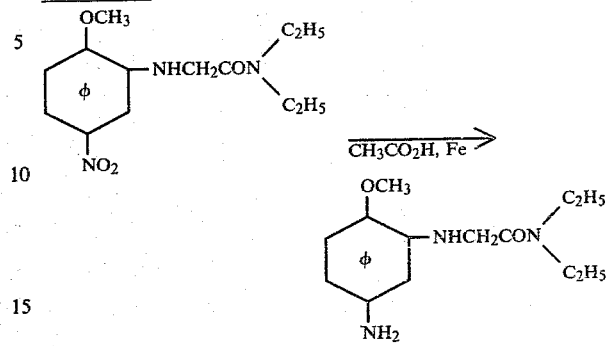

First step

Preparation of 2-diethylcarbamylmethyl anisole

Into 260 ml of hydroalcoholic solution (⅔ alcohol, ⅓ water), one adds 0.2 mol (33.6 g) of 2-amino-4-nitro anisole, 0.2 mol of calcium carbonate (20 g) and 0.4 mol (59.8 g) of N-diethyl chloroacetamide. The mixture is brought to reflux under agitation for 42 hours. It is drained while boiling and the mineral salts are washed from the precipitate with a little acetone. By cooling the filtrate, the expected product crystallizes. It is drained, washed with a little alcohol and recrystallized in alcohol. After vacuum drying it melts at 141° C.

Analysis gives the following results:

|   | Calculated for $C_{13}H_{19}N_3O_4$ | Found |
|---|---|---|
| C % | 62.15 | 61.97 |
| H % | 6.76 | 6.64 |
| N % | 14.95 | 15.20 |

Second step

Preparation of 2-diethylcarbamylmethylamino-4-amino anisole

Into 120 ml of water, one adds 28 g of iron powder and 10 ml of acetic acid. The mixture is brought to a temperature of 85° C. under agitation. Then one adds, little by little, 0.1 mol (28 g) of 2-diethylcarbamylmethylamino-4-nitro anisole. The reaction medium is maintained for 10 minutes at a temperature of 90° C. Then one adds 14 ml of 10 N. soda solution. It is filtered boiling on a heated filter. By cooling the filtrate the expected product crystallizes. After recrystallization in water and vacuum drying it melts at 111° C.

The analysis of the product gives the following results:

|   | Calculated for $C_{13}H_{21}O_2N_3$ | Found |
|---|---|---|
| C % | 62.15 | 61.97 |
| H % | 8.36 | 8.44 |
| N % | 16.73 | 16.52 |

EXAMPLE 3

The following dyeing composition is prepared:
2-carbamylmethylamino-4-amino anisole: 0.975 g Dihydrochloride of paratoluylene diamine: 1.365 g
Sodium lauryl sulfate with 19% of the initial oxyethylenated alcohol: 20 g
Product sold under the commercial name "Trilon B": 10 g
Ammonia at 22° B: 10 g
Water, q.s.: 100 g The final pH is equal to 10.5.

At the moment of use, one adds 80 g of hydrogen peroxide at 20 volumes.

This dyeing composition applied for 20 minutes at 25° C. to bleached hair imparts thereto after rinsing and shampooing a very sombre marine blue coloration.

EXAMPLE 4

The following dyeing composition is prepared:
2-carbamylmethylamino-4-amino anisole: 0.78 g
Sulfate of 4-methoxyethylamino aniline: 1.05 g
Nonylphenol having 4 mols of ethylene oxide sold under the designation "Remcopal 334" by the Gerland Company: 15 g
Nonylphenol having 9 mols of ethylene oxide sold under the designation "Remcopal 349" by the Gerland Company: 15 g
Butylglycol: 25 g
Ammonia at 22° B: 10 g
Water, q.s.: 100 g The pH is equal to 11.

At the moment of use, 50 g of hydrogen peroxide at 20 volumes is added.

This dyeing composition applied for 20 minutes at ambient temperature to the hair imparts thereto, after rinsing and shampooing, an intense royal blue coloration.

EXAMPLE 5

The following dyeing composition is prepared:
2-carbamylmethylamino-4-amino anisole: 2.7 g
4-amino-N-methoxyethyl aniline sulfate: 3.35 g
Alkyl ammonium sulfate in $C_{12}$, $C_{14}$ (70% of $C_{12}$ and 30% of $C_{14}$): 15 g
Lauric alcohol having 10.5 mols of ethylene oxide: 5 g
Ammonia at 22° B: 10 g
Water, q.s: 100 g The final pH is equal to 10.

At the moment of use, 100 g of hydrogen peroxide at 20 volumes is added.

This dyeing composition applied for 20 minutes at 25° C. to bleached hair imparts thereto, after rinsing and shampooing a marine blue coloration.

EXAMPLE 6

The following dyeing composition is prepared:
2-diethylcarbamylmethylamino-4-amino anisole: 0.20 g
Dihydrochloride of 2,6-dimethyl-3-methoxy paraphenylenediamine: 0.307 g
Butylglycol: 15 g
Nonylphenol at 4 mols of ethylene oxide: 18 g
Nonylphenol at 9 mols of ethylene oxide: 18 g
Ammonia at 22° B: 5 g
Water, q.s: 100 g The final pH is equal to 9.5.

At the moment of use, 100 g of hydrogen peroxide at 20 volumes is added.

This dyeing composition applies to bleached hair for 25 minutes at 25° C. imparts thereto, after rinsing and shampooing, a forget-me-not blue coloration.

EXAMPLE 7

The following dyeing composition is prepared:
2-carbamylmethylamino-4-amino anisole: 0.1 g
Metaaminophenol: 0.32 g
6-hydroxy benzomorpholine: 0.105 g
Dihydrochloride of 2-methyl-5-methoxy paraphenylenediamine: 0.2 g
4-amino-N,N-di-β-hydroxyethyl aniline sulfate: 0.205 g
p0 4-amino-N-methyl phenol sulfate: 0.4 g
3-nitro-4-amino-N-β-hydroxyethyl phenol: 0.3 g
Propylene glycol: 10 g
"Carbopol 934": 4.05 g
(polymer of acrylic acid, average M.W.=2 to 3 million, manufactured by the Goodrich Chemical Company)
Ammonia at 22° B: 10 g
Water, q.s.: 100 g The final pH is equal to 8.9.

At the moment of use 75 g of hydrogen peroxide at 20 volumes is added.

This dyeing composition applied to bleached hair for 15 minutes at 25° C. imparts thereto, after rinsing and shampooing, a very bright glossy maroon coloration.

EXAMPLE 8

The following dyeing composition is prepared:
2-carbamylmethylamino-4-amino anisole: 0.05 g
2-methyl-5-amino-N-β-hydroxyethyl phenol: 0.25 g
1-phenyl-3-methyl pyrazolone: 0.1 g
Dihydrochloride of 3-methyl-4-amino-N-methyl aniline: 0.4 g
4,4'-dihydroxy-2-amino-5-methyl diphenylamine: 0.55 g
2-amino-N-β-hydroxyethyl-5-nitro anisole: 0.075 g
Alcohol at 96°: 10 g
Carboxymethylcellulose: 4.25 g
Ammonia at 22° B: 5 g
Water, q.s.: 100 g The final pH is equal to 9.9.

At the moment of use, 90 g of hydrogen peroxide at 20 volumes is added.

This dyeing composition applied to bleached hair for 15 minutes at 25° C. imparts thereto, after rinsing and shampooing, a deep copper red chestnut coloration.

EXAMPLE 9

The following dyeing composition is prepared:
2-carbamylmethylamino-4-amino anisole: 0.15 g
Dihydrochloride of paratoluylenediamine: 0.60 g
4,4'-dihydroxy-2-amino-5-methyl diphenylamine: 0.55 g
4,4'-dihydroxy-2-β-hydroxyethylamino-5-methyl-2'-chloro diphenylamine: 0.25 g
Dihydrochloride of 2,6-diamino hydroquinone: 0.11 g
(3-nitro-4-amino) phenoxyethanol: 0.28 g
3-nitro-4-β-hydroxyethylamino phenol: 0.10 g
Diethanolamides of fatty acids of copra: 7.5 g
Propyleneglycol: 25 g
Ammonia at 22° B: 6 g
Water, q.s.: 100 g The pH is equal to 9.7.

At the moment of use, 90 g of hydrogen peroxide at 20 volumes is added.

This dyeing composition applied for 15 minutes at the ambient temperature to bleached hair imparts thereto, after rinsing and shampooing, a clear copper chestnut coloration.

EXAMPLE 10

The following dyeing composition is prepared:
2-carbamylmethylamino-4-amino anisole: 0.4 g
Dihydrochloride of 2,6-dimethyl-3-methoxy paraphenylenediamine: 1 g
Dihydrochloride of 4-amino-N-methoxyethyl aniline: 0.8 g
2-methyl-5-amino phenol: 0.4 g
6-hydroxy benzomorpholine: 0.4 g
3-nitro-4-amino-N-β-hydroxyethyl anisole: 0.2 g
3-nitro-4-amino-N-β-hydroxyethyl phenol: 0.05 g
Sodium lauryl sulfate with 19% of the initial oxyethylenated alcohol: 20 g
"Trilon B": 0.2 g
Ammonia at 22° B: 10 g
Water, q.s.: 100 g The final pH is equal to 10.5.

At the moment of use, 100 g of hydrogen peroxide at 20 volumes is added.

This dyeing composition applied for 20 minutes at 20° C. to bleached hair imparts thereto, after rinsing and shampooing, a very sombre grey having violet glints.

EXAMPLE 11

The following dyeing composition is prepared:
2-carbamylmethylamino-4-amino anisole: 0.15 g
Dihydrochloride of 2,6-dimethyl-3-methoxy paraphenylenediamine: 0.35 g
Dihydrochloride of 4-amino-N-methoxyethyl aniline: 0.3 g
2-methyl-5-amino phenol: 0.15 g
6-hydroxy benzomorpholine: 0.15 g
3'-nitro-4-amino-N-β-hydroxyethyl phenol: 0.01 g
3'-nitro-4-amino-N-β-hydroxyethyl anisole: 0.07 g
Sodium lauryl sulfate with 19% of the initial oxyethylenated alcohol: 20 g
"Trilon B": 0.2 g
Ammonia at 22° B: 10 g
Water, q.s.: 100 g The final pH is equal to 10.5.

At the moment of use, 100 g of hydrogen peroxide at 20 volumes is added.

This dyeing composition applied for 20 minutes at 20° C. to 95% naturally white hair imparts thereto, after rinsing and shampooing, a clear metallic grey color with light violet glints.

EXAMPLE 12

The following dyeing composition is prepared:
2-carbamylmethylamino-4-amino anisole: 0.2 g
Dihydrochloride of 2,6-dimethyl-3-methoxy paraphenylenediamine: 0.3 g
4-amino-N-ethyl-N-carbamylmethyl aniline: 1.8 g
2-methyl-5-hydroxyethylamino phenol: 0.3 g
Resorcin: 1 g
2-amino-N-β-hydroxyethyl-5-nitro anisole: 0.2 g
3-nitro-4-amino-N-β-hydroxyethyl phenol: 0.2 g
Sodium lauryl sulfate with 19% of the initial ethylenated alcohol: 20 g
"Trilon B": 0.2 g
Ammonia at 22° B: 10 g
40% sodium bisulfite: 1 g
Water, q.s.: 100 g The final pH is 10.5.

At the moment of use, 100 g of hydrogen peroxide at 20 volumes is added.

This dyeing composition applied to bleached hair for 15 minutes at 25° imparts thereto, after rinsing and shampooing, a reddish brown chestnut with golden glints.

EXAMPLE 13

The following dyeing composition is prepared:
Dihydrochloride of 2,6-dimethyl paraphenylenediamine: 0.2 g
Dihydrochloride of 2,5-diamino pyridine: 0.4 g
2-carbamylmethylamino-4-amino anisole: 0.1 g
3-amino-4-methoxy phenol: 0.15 g
2,6-dimethyl-3-acetylamino phenol: 0.05 g
(3-nitro-4-amino) phenoxyethanol: 0.13 g
1-amino-N-methyl-3-nitro-4-amino-N'-β-hydroxyethyl benzene: 0.20 g
Oleic alcohol oxyethylenated with 2 mols of ethylene oxide: 3.42 g
Oleic alcohol oxyethylenated with 4 mols of ethylene oxide: 5.09 g
Propylene glycol: 6.85 g
Ammonia at 22° B: 7.5 g
Water, q.s.: 100 g At the moment of use one adds g of hydrogen peroxide at 20 volumes.

This dyeing composition applied for 25 minutes at 30° C. to 95% naturally white hair imparts thereto, after rinsing and shampooing, a beige grey coloration having light violet glints.

EXAMPLE 14

The following dyeing composition is prepared:
2-diethylcarbamylmethylamino-4-amino anisole: 0.005 g
Dihydrochloride of 2,6-dimethyl-3-methoxy paraphenylenediamine: 0.025 g
1-amino-N-di-β-hydroxyethyl-3-nitro-4-amino-N'-methyl benzene: 0.03 g
Butylglycol: 17.5 g
Nonyl phenol having 4 mols of ethylene oxide sold under the trade designation "Remcopal 334" by the Gerland Company: 18 g
Nonyl phenol having 9 mols of ethylene oxide sold under the designation "Remcopal 349": 18 g
Triethanolamine: 1.5 g
Water, q.s.: 100 g The final pH is equal to 8.6.

At the moment of use, 15 g of hydrogen peroxide at 20 volumes is added.

This dyeing composition applied to bleached hair having a yellowish appearance for 30 minutes at the ambient temperature, imparts thereto, after rinsing and shampooing, a nacreous white having bluish glints.

EXAMPLE 15

The following dyeing composition is prepared:
2-carbamylmethylamino-4-amino anisole: 0.025 g
Dihydrochloride of 4-amino-N-methyl aniline: 0.1 g
Hydrochloride of 2-amino-4-methoxy phenol: 0.3 g
2,4'-diamino-4-hydroxy-5-methyl diphenylamine: 0.1 g
Butylglycol: 4.85 g
Lauric alcohol oxyethylenated with 10.5 mols of ethylene oxide: 4.85 g
Triethanolamine: 3 g
Water, q.s.: 100 g The final pH is equal to 8.

At the moment of use 30 g of hydrogen peroxide at 20 volumes is added.

This dyeing composition applied for 20 minutes at ambient temperature to bleached hair imparts thereto, after rinsing and shampooing, a rosy beige coloration.

EXAMPLE 16

The following dyeing composition is prepared:
2-carbamylmethylamino-4-amino anisole: 0.0025 g
Dihydrochloride of 4-amino-N-methyl aniline: 0.06 g
2-methyl-5-amino-N-$\beta$-hydroxyethyl phenol: 0.015 g
Sodium lauryl sulfate with 19% of the initial-ethylenated alcohol: 20 g
"Trilon B" 0.2 g
40% sodium bisulfite: 1 g
Ammonia at 22° B: 10 g
Water, q.s.: 100 g The final pH is equal to 11.

At the moment of use, 10 g of hydrogen peroxide at 20 volumes is added.

This dyeing composition applied to bleached hair for 10 minutes at 25° C. imparts thereto, after rinsing and shampooing a very clear grey coloration.

EXAMPLE 17

The following dyeing composition is prepared:
2-carbamylmethylamino-4-amino anisole: 0.1 g
Dihydrochloride of 2,6-dimethyl-3-methoxy paraphenylenediamine: 0.2 g
1-amino-N-di-$\beta$-hydroxyethyl-3-nitro-4-amino-N'-methyl benzene: 0.1 g
Sodium lauryl sulfate with 19% of the initial ethylenated alcohol: 20 g
"Trilon B": 0.2 g
Ammonia at 22° B: 10 g
40% sodium bisulfite: 1 g
Water, q.s.: 100 g The final pH is equal to 10.5.

At the moment of use 100 g of hydrogen peroxide at 20 volumes is added.

This dyeing composition applied for 20 minutes at 25° C. to bleached hair imparts thereto, after rinsing and shampooing, a clear bluish grey coloration.

It is well understood that the methods of preparation and the examples of composition hereinbefore given are in no way limitative and may be modified as desired without thereby departing from the scope of the invention.

We claim:

1. A dyeing composition for keratinic fibers and particularly for hair, comprising an aqueous solution containing a dyeing amount of at least one paraphenylenediamene oxidation base, and as a coupler, at least one compound having the general formula (I):

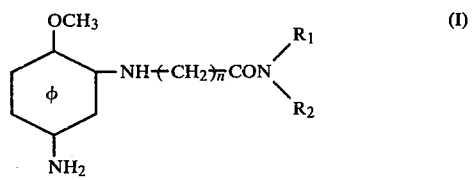

in which $R_1$ and $R_2$ are hydrogen and n is equal to 1.

2. The composition of claim 1, in which the paraphenylenediamine or paraphenylenediamines used as the oxidation base or bases correspond to the general formula (II):

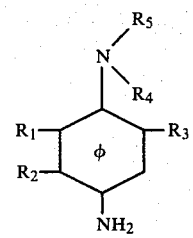

or the corresponding acid salts, in which formula $R_1$, $R_2$, $R_3$ are identical or different and represent hydrogen, alkyl or alkoxy having 1 to 2 carbon atoms, $R_4$ and $R_5$ are identical or different and selected from the group consisting of hydrogen, alkyl, hydroxyalkyl, alkoxyalkyl in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 carbon atoms with the reservation that $R_1$ and $R_2$ represent hydrogen when $R_4$ and $R_5$ do not represent hydrogen.

3. The composition of claim 1, which has as an oxidation base, a base selected from the group consisting of paraphenylenediamine, paratoluylenediamine, 2,6-dimethyl-3-methoxy paraphenylenediamine, 2-methyl-5-methoxy paraphenylenediamine, 2,6-dimethyl paraphenylenediamine, 4-amino-N-methoxyethyl aniline, 4-amino-N,N-di$\beta$-hydroxyethyl aniline, 4-amino-N-ethyl-N-carbamylmethyl aniline, 4-amino-N-ethyl-N-mesylaminoethyl aniline.

4. The composition of claim 1 which contains at least one coupler other than those of formula (I).

5. The composition of claim 4 in which the coupler, or couplers, other than those of formula (I) are selected from the group consisting of resorcin, metaaminophenol, 2-methyl-5-amino phenol, 2-methyl-5-amino-N-$\beta$-hydroxyethyl phenol, 6-hydroxy benzomorpholine, 2,6-dimethyl-5-acetylamino phenol, 2-methoxy-5-carbethoxyamino phenol, 2-methyl-5-ureido phenol, 3-amino-4-methoxy phenol, the dihydrochloride of (2,4-diamino) phenoxyethanol, the dihydrochloride of (2-amino-4-amino-N-methyl)phenoxyethanol, the dihydrochloride of (2,4-diamino) phenyl-$\beta$-methoxyethylether and the dihydrochloride of (2,4-diamino) phenyl-mesylaminoethylether.

6. The composition of claim 1 which also contains the leucoderivatives of indoanilines and indophenols.

7. The composition of claim 1 which also contains at least one compound selected from the group consisting of monoaminodiphenols, diaminodiphenols and polyphenols.

8. The composition of claim 1 which also contains at least one direct dye.

9. The composition of claim 8 in which the direct dye or dyes are the nitrated dyes of the benzene series.

10. The composition of claim 9 in which the nitrated dyes of the benzene series are selected from the group consisting of 1-amino-N,N-dihydroxyethyl-3-nitro-4-amino-N'-methyl benzene, 1-amino-N,N-(methyl-$\beta$-hydroxyethyl)-3-nitro-4-amino-N'-$\beta$-hydroxyethyl benzene, 1-amino-N,N-(methyl-$\beta$-hydroxyethyl)-3-nitro-4-amino-N'-methyl benzene, 1-amino-N-methyl-3-nitro-4-amino-N'-$\beta$-hydroxyethyl benzene, 3-nitro-4-amino-N-$\beta$-hydroxyethyl anisole, 3-nitro-4-amino-N-$\beta$-hydroxyethyl phenol, (3-nitro-4-amino) phenoxyethanol, (3-nitro-4-amino-N-methyl)phenoxyethanol, 2-$\beta$-hydroxyethylamino-5-nitro anisole and 2-methyl-4-nitro aniline.

11. The composition of claim 1, which also contains at least one additive selected from the group consisting of penetrating agents, foaming agents, thickening agents, anti-oxidizing agents, alkalizing agents, perfumes, sequestrating agents and film forming products.

12. The composition of claim 1 which has a pH between 8 and 11.5.

13. The composition of claim 1 which contains at least one compound of formula (I) in a proportion between 0.0025 and 2.5% in proportion to the total weight of the composition.

14. The composition of claim 6 in which said leucoderivatives are selected from the group consisting of 4,4'-dihydroxy-2-amino-5-methyl diphenylamine, 4,4'-dihydroxy-2-amino-N-β-hydroxyethyl-5-methyl-2'-chloro diphenylamine and 2,4'-diamino-4-hydroxy-5-methyl diphenylamine.

* * * * *